US007214703B2

(12) United States Patent
Anderskewitz et al.

(10) Patent No.: US 7,214,703 B2
(45) Date of Patent: May 8, 2007

(54) PYRROLIDINOHYDROCHINAZOLINES

(75) Inventors: Ralf Anderskewitz, Laupheim (DE); Horst Dollinger, Schemmerhofen (DE); Claudia Heine, Biberach (DE); Pascale Arielle Jane-Josee Pouzet, Biberach (DE); Thierry Bouyssou, Mietingen (DE); Franz Birke, Ingelheim (DE)

(73) Assignee: Boehringer Ingelheim International GmbH (DE)

( * ) Notice: Subject to any disclaimer, the term of this patent is extended or adjusted under 35 U.S.C. 154(b) by 307 days.

(21) Appl. No.: 10/771,756

(22) Filed: Feb. 4, 2004

(65) Prior Publication Data

US 2005/0027122 A1 Feb. 3, 2005

Related U.S. Application Data

(60) Provisional application No. 60/499,529, filed on Sep. 2, 2003.

(30) Foreign Application Priority Data

Feb. 12, 2003 (EP) .................................. 03003007

(51) Int. Cl.
*A01N 43/38* (2006.01)
*A61K 31/40* (2006.01)
*C07D 487/02* (2006.01)

(52) U.S. Cl. ...................... 514/413; 514/408; 514/410; 514/412; 548/416; 548/452; 548/453

(58) Field of Classification Search ................ 514/408, 514/410, 412, 413; 548/416, 452, 453
See application file for complete search history.

(56) References Cited

OTHER PUBLICATIONS

Molina, Pedro et al; Inhibition of Leucocyte functions by the alkalols isaindigotone from Isatis indigotica and some new synthetic derivatives, Journal of Natural Products, vol. 64, No. 10, 2001, XP002286635, example 1.

Rioja, Immaculada, et al; "A pyrroloquinazoline derivative with antiinflammatory and analgesic activity by dual inhibition of COX-2 and 5-lipooxygenase" European Journal of Pharmacology, vol. 434, No. 10, 2002, XP 002286636 figures, example 1.

*Primary Examiner*—James O. Wilson
*Assistant Examiner*—Paul V. Ward
(74) *Attorney, Agent, or Firm*—Michael Morris; Mary-Ellen M. Devlin; Anthony P. Bottino

(57) ABSTRACT

Disclosed are compounds of formula (I):

(I)

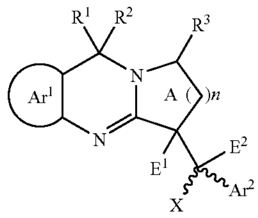

, or stereoisomers or pharmaceutically acceptable salts thereof, wherein the groups $Ar^1$, $Ar^2$, A, $R^1$, $R^2$, $R^3$, $E^1$, $E^2$, X and n are as defined in the description and claims, which are effective modulators of chemokine activity.

8 Claims, No Drawings

PYRROLIDINOHYDROCHINAZOLINES

RELATED APPLICATION DATA

This application claims benefit to EP 03003007.6 filed Feb. 12, 2003 and U.S. provisional application No. 60/499, 529 filed Sep. 2, 2003.

BACKGROUND OF THE INVENTION

1. Technical Field

This invention relates generally to novel pyrrolidinohydrochinazolines and their use as modulators of chemokine receptor activity, pharmaceutical compositions containing the same, and methods of using the same as agents for treatment and prevention of inflammatory diseases such as asthma and allergic diseases, as well as autoimmune pathologies such as rheumatoid arthritis and atherosclerosis.

2. Background Information

Chemokines are chemotactic cytokines, of molecular weight 6–15 kDa, that are released by a wide variety of cells to attract and activate, among other cell types, macrophages, T and B lymphocytes, eosinophils, basophils and neutrophils (reviewed in Luster, New Eng. J Med., 338, 436–445 (1998) and Rollins, Blood, 90, 909–928 (1997)).

There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP2) and melanoma growth stimulatory activity protein (MGSA) are chemotactic primarily for neutrophils and T lymphocytes, whereas the CC chemokines, such as RANTES, MIP-1a, MIP-1 (3, the monocyte chemotactic proteins (MCP-1, MCP-2, MCP-3, MCP-4, and MCP-5) and the eotaxins (-1, -2, and -3) are chemotactic for, among other cell types, macrophages, T lymphocytes, eosinophils, dendritic cells, and basophils. There also exist the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seventrans-membrane-domain proteins (reviewed in Horuk, Trends Pharm. Sci., 15, 159–165 (1994)) which are termed "chemokine receptors." On binding their cognate ligands, chemokine receptors transduce an intracellular signal through the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns: CCR1 (or "CKR-1" or "CC-CKR-1") [MIP-1a, MCP-3, MCP-4, RANTES] (Ben-Barruch, et al., Cell, 72, 415–425 (1993), Luster, New Eng. J. Med., 338, 436–445 (1998)); CCR-2A and CCR-2B (or "CKR-2A"/"CKR-2B" or "CC-CKR-2A"/"CC-CKR-2B") [MCP-1, MCP2, MCP-3, MCP-4, MCP-5] (Charo et al., Proc. Natl. Acad. Sci. USA, 91, 2752–2756 (1994), Luster, New Eng. J. Med., 338, 436–445 (1998)); CCR-3 (or "CKR-3" or "CC-CKR-3") [eotaxin-1, eotaxin-2, RANTES, MCP-3, MCP-4] (Combadiere, et al., J. Biol. Chem., 270, 16491–16494 (1995), Luster, New Eng. J. Med., 338,436–445 (1998)); CCR-4 (or "CKR-4" or "CC-CKR-4") [TARC, MIP-1a, RANTES, MCP-1] (Power et al., J. Biol. Chem., 270, 19495–19500 (1995), Luster, New Eng. J. Med., 338, 436–445 (1998)); CCR-5 (or "CKR-5" OR "CCCKR-5") [MIP-1a, RANTES, MIP-1p] (Sanson, et al., Biochemistry, 35, 3362–3367 (1996)); CCR-6 (or "CKR-6" or "CC-CKR-6") [LARC] (Baba et al., J. Biol. Chem., 272, 14893–14898 (1997)); CCR-7 (or "CKR-7" or "CC-CKR-7") [ELC] (Yoshie et al., J. Leukoc. Biol. 62, 634–644 (1997)); CCR-8 (or "CKR-8" or "CC-CKR-8") [1–309, TARC, MIP-1p] (Napolitano et al., J. Immunol., 157, 2759–2763 (1996), Bernardini et al., Eur. J. Immunol., 28, 582–588 (1998)); and CCR-10 (or "CKR-10" or "CC-CKR-10") [MCP-1, MCP-3] (Bonini et al, DNA and Cell Biol., 16, 1249–1256 (1997)).

In addition to the mammalian chemokine receptors, mammalian cytomegaloviruses, herpesviruses and poxviruses have been shown to express, in infected cells, proteins with the binding properties of chemokine receptors (reviewed by Wells and Schwartz, Curr. Opin. Biotech., 8, 741–748 (1997)). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as coreceptors for the infection of mammalian cells by microbes as with, for example, the human immunodeficiency viruses (HIV).

Chemokine receptors have been implicated as being important mediators of inflammatory, infectious, and immunoregulatory disorders and diseases, including asthma and allergic diseases, as well as autoimmune pathologies such as rheumatoid arthritis and atherosclerosis. For example, the chemokine receptor CCR-3 plays a pivotal role in attracting eosinophils to sites of allergic inflammation and in subsequently activating these cells. The chemokine ligands for CCR-3 induce a rapid increase in intracellular calcium concentration, increased expression of cellular adhesion molecules, cellular degranulation, and the promotion of eosinophil migration. Accordingly, agents which modulate chemokine receptors would be useful in such disorders and diseases. In addition, agents which modulate chemokine receptors would also be useful in infectious diseases such as by blocking infection of CCR3 expressing cells by HIV or in preventing the manipulation of immune cellular responses by viruses such as cytomegaloviruses.

The prior art does not disclose nor suggest the unique structure of the novel pyrrolidinohydrochinazolines nor that they might have activity toward the chemokine receptors.

BRIEF SUMMARY OF THE INVENTION

Accordingly, one object of the present invention is to provide agonists or antagonists of CCR-3, or pharmaceutically acceptable salts thereof, in particular pyrrolidinohydrochinazolines of formula (I):

(I)

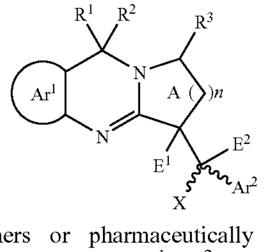

, or stereoisomers or pharmaceutically acceptable salts thereof, wherein the groups $Ar^1$, $Ar^2$, A, $E^1$, $E^2$, $R^1$, $R^2$, $R^3$, X and n are defined below.

It is another object of the present invention to provide pharmaceutical compositions comprising a pharmaceutically acceptable carrier and a therapeutically effective amount of at least one of the compounds of the present invention or a pharmaceutically acceptable salt thereof.

It is another object of the present invention to provide a method for treating inflammatory diseases and allergic disorders comprising administering to a host in need of such treatment a therapeutically effective amount of at least one of the compounds of the present invention or a pharmaceutically acceptable salt thereof.

These and other objects, which will become apparent during the following detailed description.

DETAILED DESCRIPTION OF THE INVENTION

The present invention relates to the novel compounds of formula (I):

(I)

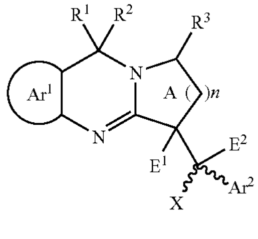
, wherein $R^1$ and $R^2$ each independently represent a hydrogen atom, or a $C_1$–$C_6$-alkyl, $C_2$–$C_6$-alkenyl, $C_2$–$C_6$-alkynyl, $C_3$–$C_8$-cycloalkyl, $C_3$–$C_8$-cycloalkyl-$C_1$–$C_6$-alkyl, —$NH_2$, —NH($C_1$–$C_6$-alkyl), —N($C_1$–$C_6$-alkyl)$_2$, aryl or aryl-$C_1$–$C_6$-alkyl group, wherein any of these groups may optionally be substituted by one or more substituents selected from the group consisting of halogen, $OR^6$, $SR^6$, cyano, $COOR^6$, $CONR^6R^7$, $NR^6R^7$, $NR^6COR^5$, $SOR^6$, $SO^2R^6$ and $C_1$–$C_6$-haloalkyl, $R^1$ and $R^2$ together with the intedjacent carbon atom form a 3- to 8-membered cycloalkyl ring, which may be substituted by one or more substituents selected from the group consisting of halogen, $C_1$–$C_6$-alkyl, $OR^6$, $SR^6$ and cyano, $C_1$–$C_6$-haloalkyl or $R^1$ and $R^2$ form together a group $=NR^4$;

$R^3$ represents a hydrogen atom or a $C_1$–$C_{18}$-alkyl, $C_2$–$C_6$-alkenyl, $C_2$–$C_6$-alkinyl, $C_3$–$C_8$-cycloalkyl, $C_3$–$C_8$-cycloalkyl-$C_1$–$C_6$-alkyl, aryl, or aryl-$C_1$–$C_6$-alkyl, $COOR^5$, $CR^6R^7OH$ or $CONR^6R^7$ group, wherein any of these groups may optionally be substituted by one or more substituents selected from the group consisting of halogen, $OR^6$, $SR^6$, CN, $COOR^6$, $CONR^6R^7$, $NR^6R^7$, $NR^6COR^5$, $SOR^6$, $SO_2R^6$ and $C_1$–$C_6$-haloalkyl;

$R^4$ represents a hydrogen atom or a $COOR^5$, $COR^5$, $OR^6$, cyano or nitro group; or a $C_1$–$C_6$-alkyl group, which, may optionally be substituted by one or more substituents selected from the group consisting of halogen, $OR^6$, $SR^6$, CN, $COOR^6$, $CONR^6R^7$, $NR^6R^7$, $NR^6COR^5$, $SOR^6$, $SO^2R^6$ and $C_1$–$C_6$-haloalkyl; or $R^2$ and $R^3$ together with the intedjacent group —$CR^1$—N—CH— form a 5- to 8-membered ring; or $R^3$ and $R^4$ together with the intedjacent group —N═C—N—CH— form a 5- to 8-membered ring;

$R^5$ represents a hydrogen atom or a $C_1$–$C_{18}$-alkyl, $C_2$–$C_6$-alkenyl, $C_2$–$C_6$-alkinyl, $C_3$–$C_8$-cycloalkyl, $C_3$–$C_8$-cycloalkyl-$C_1$–$C_6$-alkyl, aryl or aryl-$C_1$–$C_6$-alkyl group, wherein any of these groups may optionally be substituted by one or more substituents selected from the group consisting of halogen, $OR^6$, $SR^6$, CN, $COOR^6$, $CONR^6R^7$, $NR^6R^7$, $NR^6COR^5$, $SOR^6$, $SO_2R^6$ and $C_1$–$C_6$-haloalkyl;

$R^6$ and $R^7$ each independently represent a hydrogen atom, or a $C_1$–$C_{18}$-alkyl, $C_3$–$C_8$-cycloalkyl aryl or aryl-$C_1$–$C_6$-alkyl group; or $R^6$ and $R^7$ together with the interjacent nitrogen atom form a 3–8-membered heterocyclic ring;

$E^1$ and $E^2$ each represent a hydrogen atom or taken together form a double bond;

X represents a hydrogen or halogen atom, or a $C_1$–$C_6$-alkyl, $C_2$–$C_6$-alkenyl, $C_2$–$C_6$-alkinyl, $C_3$–$C_8$-cycloalkyl, $C_3$–$C_8$-cycloalkyl-$C_1$–$C_6$-alkyl, $OR^6$, $SR^6$, $NR^6R^7$ or aryl;

the ring A may be substituted by one or more group $R^6$;

Aryl, $Ar^1$ and $Ar^2$ each independently represent a 6- to 10-membered homoaromatic group or a 5- to 10-membered heteroaromatic group containing up to three heteroatoms selected from the group consisting of nitrogen, oxygen and sulfur; wherein each of these groups may be substituted by one or more substituents selected from the group consisting of $C_1$–$C_6$-alkyl, phenyl, halogen, $OR^6$, $SR^6$, cyano, nitro, $COOR^6$, $COR^6$, $CONR^6R^7$, $NR^6R^7$, $NR^6COR^5$, $NR^6SO_2R^5$, $SOR^6$, $SO_2R^6$, $SO_2NR^6R^7$, $C_1$–$C_6$-haloalkoxy and $C_3$–$C_8$-cycloalkyl; and n represents an integer from 1 to 4.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C═N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted" as used herein, means that any one or more hydrogens on the designated atom is replaced with a selection from the indicated group, provided that the designated atom's normal valency is not exceeded, and that the substitution results in a stable compound. When a substitent is keto (i. e., ═O), then 2 hydrogens on the atom are replaced.

When any substituent occurs more than one time in any constituent or formula for a compound, its definition at each occurrence is independent of its definition at every other occurrence. Thus, for example, if a group is shown to be substituted with 0–2 substituents, then said group may optionally be substituted with up to two such substituents which at each occurrence is selected independently from the definitions of said substituents. Also, combinations of substituents and/or variables are permissible only if such combinations result in stable compounds.

As used herein, "alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl. The term "$C_1$–$C_6$ alkyl" is intended to include all C1, C2, C3, C4, C5, and C6 alkyl groups.

"Alkenyl" is intended to include hydrocarbon chains of either a straight or branched configuration and one or more unsaturated carbon-carbon bonds which may occur in any stable point along the chain, such as ethenyl, propenyl, and the like. "Alkynyl" is intended to include hydrocarbon chains of either a straight or branched configuration and one or more unsaturated triple carbon-carbon bonds which may occur in any stable point along the chain, such as ethynyl, propynyl, and the like. "$C_3$–$C_8$ cycloalkyl" is intended to include saturated ring groups having the specified number of carbon atoms in the ring, including mono-, bi-, or polycyclic ring systems, such as cyclopropyl, cyclobutyl, cyclopentyl, cyclohexyl and cycloheptyl. $C_3$–$C_8$ cycloalkyl, is intended to include C3, C4, C5, and C6 cycloalkyl groups.

"Halo" or "halogen" as used herein refers to fluoro, chloro, bromo, and iodo; "haloalkyl" is intended to include both branched and straight-chain halogenated, in particular fluorinated, saturated aliphatic hydrocarbon groups, for example $CF_3$, $C_2F_5$, $CH_2CF_3$ and 1,1,1-trifluoroprop-2-yl, having the specified number of carbon atoms, substituted with 1 or more halogen (for example—$C_vF_wH_{2v+1-w}$ where v=1 to 3 and w=1 to (2v+1)); and "haloalkoxy" is intended to include both branched and straight-chain halogenated, in particular fluorinated, saturated aliphatic alkoxy groups, for example $OCHF_2$, $OCF_3$, $OC_2F_5$, $OCH_2CF_3$ and 1,1,1-trifluoroprop-2-yloxy, having the specified number of carbon atoms, substituted with 1 or more halogen (for example—O—$C_vF_wH_{2v+1-w}$ where v=1 to 3 and w=1 to (2v+1)).

The compounds of formula (I) can also be quaternized by standard techniques such as alkylation of the amino group $NR^6R^7$ with an alkyl halide to yield quaternary piperidinium salt products of formula I. Such quaternary ammonium salts would include a counterion. As used herein, "counterion" is used to represent a small, negatively charged species such as chloride, bromide, hydroxide, acetate, sulfate, and the like.

As used herein the term "homoaromatic group" is intended to mean a 6- to 10 membered monocyclic or bicyclic aromatic group, which does not comprise any heteroatom within the ring moiety. Preferred is phenyl and naphthyl, in particular phenyl.

As used herein, the term "heterocyclic group" is intended to mean a stable 5-, 6-, or 7-membered monocyclic or 7, 8, 9, or 10-membered bicyclic heterocyclic ring which is saturated or partially unsaturated, and which consists of carbon atoms and 1, 2, or 3 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring is attached to its pendant group at the nitrogen atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another.

Examples of heterocycles include, but are not limited to, 1H-indazole, 2-pyrrolidonyl, 2H, 6H-1,5,2-dithiazinyl, 2H-pyrrolyl, 3H-indolyl, 1-piperidinyl, 1-piperazinyl, 1-morpholinyl.

As used herein, the term "heteroaromatic group" is intended to mean a stable 5-, or 6-, membered monocyclic or 7, 8, 9, or 10-membered bicyclic heteroaromatic ring which is fully unsaturated, and which consists of carbon atoms and 1, 2, or 3 heteroatoms independently selected from the group consisting of N, O and S and including any bicyclic group in which any of the above-defined heteroaromatic rings is fused to a benzene ring. The heteroaromtic ring is attached to its pendant group at a carbon atom which results in a stable structure. The heteroaromatic rings described herein may be substituted on carbon or on a nitrogen atom if the resulting compound is stable. If specifically noted, a nitrogen in the heteroaromatic group may optionally be quaternized.

Examples of heterocycles include, but are not limited to, thienyl, furanyl, pyrrolyl, pyridyl, pyrimidyl, pyridazyl, triazinyl, benzothiophenyl, indolyl, thiazolyl, oxazolyl, pyrazolyl, imidazolyl, triazolyl and tetrazolyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from nontoxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remingto which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

Preferred are the compounds of formula I, wherein

Aryl, $Ar^1$ and $Ar^2$ each independently are selected from the group consisting of phenyl, thienyl, furanyl, pyrrolyl, pyridyl, pyrimidyl, naphthyl, benzothiophenyl, indolyl, thiazolyl, oxazolyl and imidazolyl, wherein each of these groups may be substituted by one two or three substituents selected from the group consisting of $C_1$–$C_6$-alkyl, phenyl, halogen, $OR^6$, $SR^6$, cyano, nitro, $COOR^6$, $COR^6$, $CONR^6R^7$, $NR^6R^7$, $NR^6COR^5$, $NR^6SO_2R^5$, $SOR^6$, $SO_2NR^6R^7$, $C_1$–$C_6$-haloalkyl, $C_1$–$C_6$-haloalkoxy and $C_3$–$C_8$-cycloalkyl, in particular phenyl, thienyl and furanyl, wherein each of these groups may be substituted by one or two substituents selected from the group consisting of $C_1$–$C_3$-alkyl, phenyl, fluorine, chlorine, bromine, $OR^6$, cyano, nitro, $COOR^6$, $COR^6$, $CONR^6R^7$, $NR^6R^7$, $NR^6COR^5$, $C_1$–$C_3$-fluoroalkyl, $C_1$–$C_3$-fluoroalkoxy and $C_3$–$C_8$-cycloalkyl; and/or wherein $E^1$ and $E^2$ taken together form a double bond.

Furthermore preferred are those compounds of formula I, wherein $R^1$ and $R^2$ each independently represent a hydrogen atom, or a $C_1$–$C_6$-alkyl group, $R^1$ and $R^2$ form together a group $=NR^4$;

$R^3$ represents a hydrogen atom or a $C_1$–$C_{18}$-alkyl group, $R^4$ represents a hydrogen atom, or a $C_1$–$C_6$-alkyl or cyano group, $E^1$ and $E^2$ taken together form a double bond;

$Ar^1$ represents a phenyl, thiophene or furane group, which may be substituted by one or more substituents selected from the group consisting of $C_1$–$C_6$-alkyl, phenyl,halogen, $OR^6$, $SR^6$, cyano, nitro, $COOR^6$, $COR^6$, $CONR^6R^7$, $NR^6R^7$, $NR^6COR^5$, $NR^6SO_2R^5$, $SOR^6$, $SO_2R^6$, $C_1$–$C_6$-haloalkyl, $C_1$–$C_6$-haloalkoxy and $C_3$–$C_8$-cycloalkyl, $Ar^2$ represents a phenyl, thienyl or furanyl group, which may be substituted by one or more substituents selected from the group consisting of $C_1$–$C_6$-alkyl, phenyl, halogen, $OR^6$, $SR^6$, cyano, nitro, $COOR^6$, $COR^6$, $CONR^6R^7$, $NR^6R^7$, $NR^6COR^5$, $NR^6SO_2R^5$, $SOR^6$, $SO_2R^6$, $SO_2NR^6R^7$, $C_1$–$C_6$-haloalkyl, $C_1$–$C_6$-haloalkoxy and $C_3$–$C_8$-cycloalkyl; and n represents 1 or 2.

Particularly preferred are the compounds of formula I, wherein $R^1$ and $R^2$ represent a hydrogen atom, or $R^1$ and $R^2$ form together a group $=NR^4$;

$R^3$ and $R^4$ each independently represent a hydrogen atom or a $C_1$–$C_6$-alkyl group, $E^1$ and $E^2$ taken together form a double bond;

$Ar^1$ represents a phenyl, thiophene or furane group, which may be substituted by one or more substituents selected from the group consisting of $C_1$–$C_6$-alkyl, halogen, $C_1$–$C_6$-haloalkyl and $C_3$-$C_6$-cycloalkyl, $Ar^2$ represents a phenyl, thienyl or furanyl group, which may be substituted by a halogen atom, n represents 1; and X represents a hydrogen atom.

Most preferred are the compounds of formula I, wherein $Ar^2$ represents a phenyl, thienyl or furanyl group, which is substituted by a halogen atom, in the ortho position.

The compounds of formula I can be prepared using the reactions and techniques described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (Protective Groups In Organic Synthesis, Wiley and Sons, 1991).

Preferably, the compounds of formula I are prepared by reaction of a compound of formula (II)

(II)

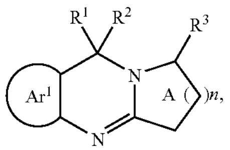

wherein $Ar^1$, A, $R^1$, $R^2$, $R^3$ and n have the meaning given hereinabove, with a compound of formula (III)

(III)

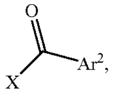

wherein $Ar^2$ and X have the meaning given hereinabove, and optionally followed by hydrogenation ($E^1$=$E^2$=H).

The compounds of formula (II), in which $R^1$ and $R^2$ are different from $=NR^4$, may be obtained for example by the reaction of a diamino compound of formula (IV)

(IV)

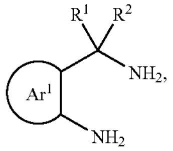

with a lactone of formula (V)

(V)

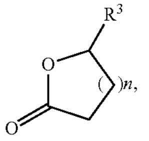

in the presence of a dehydrating agent such as $POCl_3$.

The compounds of formula (II), in which $R^1$ and $R^2$ together represent $=NR^4$, may be obtained for example by the reaction of an 1-amino-2-cyano compound of formula (VI)

(VI)

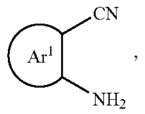

with a compound of formula (VII)

(VII)

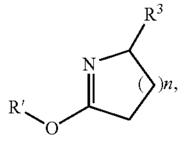

in which $R^3$ and n have the meaning given and R' represents $C_{1-6}$ alkyl, optionally in the presence of an inert diluent at elevated temperatures, preferably at temperatures below 200° C., in particular from 70° C. to 150° C.

The utility of the compounds in accordance with the present invention as modulators of chemokine receptor activity may be demonstrated by methodology known in the art, such as the assays for CCR-2 and CCR-3 ligand binding, as disclosed by Ponath et al., J. Exp. Med., 183, 2437–2448 (1996) and Uguccioni et al., J. Clin. Invest., 100, 11371143 (1997). Cell lines for expressing the receptor of interest include those naturally expressing the chemokine receptor, such as EOL-3 or THP-1, those induced to express the chemokine receptor by the addition of chemical or protein agents, such as HL-60 or AML14.3D10 cells treated with, for example, butyric acid with interleukin-5 present, or a cell engineered to express a recombinant chemokine receptor, such as CHO or HEK-293. Finally, blood or tissue cells, for example human peripheral blood eosinophils, isolated using methods as described by Hansel et al., J. Immunol. Methods, 145, 105–110 (1991), can be utilized in such assays. In particular, the compound of the present invention have activity in binding to the CCR-3 receptor in the aforementioned assays. As used herein, "activity" is intended to mean a compound demonstrating an IC50 of 10 MM or lower in concentration when measured in the aforementioned assays. Such a result is indicative of the intrinsic activity of the compounds as modulators of chemokine receptor activity. A general binding protocol is described below.

CCR3-Receptor Binding Protocol

The CCR3 receptor binding test is based on a K562 cell line (leukemia myelogenic blast cells ) transfected with the human chemokine receptor CCR3 (hCCR3-C1). The cell membranes were prepared by disrupting the hCCR3 transfected K562 cells by nitrogen decomposition and centrifugation at 40000 g, 4° C. for 1 h. The membranes were re-suspended in the SPA incubation buffer (see below) without bovine serum albumin for storage in aliquots at −80° C.

The CCR3 receptor binding assay with the radioligand $^{125}$Jodine-eotaxin-1 was performed in a Scintillation Proximity Assay (SPA) design. Cell membranes of hCCR3 C1 cells were diluted in suitable concentrations (0.5–5 ug protein/well ) in 96 well microtiter plates (1450–401, Wallac).

The test incubation mixture comprising 60 μl of the membrane suspension, 80 μl of the Wheat Germ Agglutinin coated PVT beads (organic scintillator, Amersham Pharmacia biotech) in a concentration of 0.4 mg and 40 μl of radiolabelled $^{125}$J rhEotaxin (Amersham, IM290) were incubated with 20 μl of the test compound (dissolved in DMSO dilutions ) for 2 hours. The SPA incubation buffer contained 25 mM HEPES, 25 mM $MgCl_2$ $6{\times}H_2O$, 1 mM $CaCl_2$ $2{\times}H_2O$ and 0.1% bovine serum albumin. Included were controls for specific binding (no displacer added) and non-specific binding by adding unlabelled rhEotaxin (R&D Systems) or a test compound. Bound radioactivity was determined by scintillation counter (Micro Beta "Trilux", Wallac). Determination of affinity of test compounds (dissociation constant $K_i$) was calculated by iterative fitting of experimental data using the law of mass action based program "easy sys" (Schittkowski, Num Math 68, 129–142 (1994)).

The utility of the compounds in accordance with the present invention as inhibitors of the migration of eosinophils or cell lines expressing the chemokine receptors may be demonstrated by methodology known in the art, such as the chemotaxis assay disclosed by Bacon et al., Brit. J. Pharmacol., 95, 966–974 (1988). In particular, the compound of the present invention have activity in inhibition of the migration of eosinophils in the aforementioned assays. As used herein, "activity" is intended to mean a compound demonstrating an $K_i$ of 10 μM or lower in concentration when measured in the aforementioned assays. Such a result is indicative of the intrinsic activity of the compounds as modulators of chemokine receptor activity. Mammalian chemokine receptors provide a target for interfering with or promoting immune cell function in a mammal, such as a human. Compounds that inhibit or promote chemokine receptor function are particularly useful for modulating immune cell function for therapeutic purposes.

Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e. g., a human chemokine receptor) may be administered to inhibit (i. e., reduce or prevent) inflammation or infectious disease. As a result, one or more inflammatory process, such as leukocyte emigration, adhesion, chemotaxis, exocytosis (e. g., of enzymes, histamine) or inflammatory mediator release, is inhibited. For example, eosinophilic infiltration to inflammatory sites (e. g., in asthma or allergic rhinitis) can be inhibited according to the present method. In particular, the compound of the following examples has activity in blocking the migration of cells expressing the CCR-3 receptor using the appropriate chemokines in the aforementioned assays.

Similarly, an instant compound which promotes one or more functions of the mammalian chemokine receptor (e. g., a human chemokine) as administered to stimulate (induce or enhance) an immune or inflammatory response, such as leukocyte emigration, adhesion, chemotaxis, exocytosis (e. g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e. g., Well's syndrome), eosinophilic pneumonias (e. g., Loeffler's syndrome, chronic eosinophilic pneumonia), eosinophilic fasciitis (e. g., Shulman's syndrome), delayed-type hypersensitivity, interstitial lung diseases (ILD) (e. g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e. g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e. g., in transplantation), including allograft rejection or graftversus-host disease; inflammatory bowel diseases, such as Crohn's disease and ulcerative colitis; spondyloarthropathies; scleroderma; psoriasis (including Tcell mediated psoriasis) and inflammatory dermatoses such as an dermatitis, eczema, atopic dermatitis, allergic contact dermatitis, urticaria; vasculitis (e. g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e. g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e. g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e. g., Toxocara), eosinophilic gastroenteritis (e. g., Anisaki sp., Phocanema sp.), cutaneous larva migraines (Ancylostona braziliense, Ancylostoma caninum). The compounds of the present invention are accordingly useful in the prevention and treatment of a wide variety of inflammatory, infectious and immunoregulatory disorders and diseases. In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness.

Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a nonsteroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or nonsedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) nonsteroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY-1005); (f) nonsteroidal antiinflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, meloxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (I) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (1) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (o) other compound such as 5-aminosalicylic acid an prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of formula I that, when administered alone or in combination with an additional therapeutic agent to a mammal, is effective to prevent or ameliorate the thromboembolic disease condition or the progression of the disease.

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues.

Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit.

In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in Remington's Pharmaceutical Sciences, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U. S. P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients.

Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

As will be appreciated by one of skill in the art, numerous modifications and variations of the present invention are possible in light of the above teachings. It is therefore to be understood that within the scope of the appended claims, the invention may be practiced otherwise than as specifically described herein.

EXAMPLE 101

3-(2-Bromobenzylidene)-1,2,3,9-tetrahydro-pyrrolo[2,1-b]quinazoline a) A mixture of 61.1 g of 2-amino-benzylamine and 47.35 γ-butyrolactone are stirred for 2 hrs. at 200° C., cooled down and diluted with 100 ml toluene. The mixture is heated under reflux and concentrated. 200 ml of $POCl_3$ are added to the residue and heated under reflux for 2 hrs. Remaining $POCl_3$ is distilled off, the residue is hydrolyzed and alkalized with a 32% solution of NaOH. The resulting solution is extracted 3 times with 700 ml of dichloromethane, the combined organic phases are washed with water twice. The organic phase is dried over $MgSO_4$ and concentrated. The remaining oil solidifies within a short time to yield: 55 g of crude 1,2,3,9-tetrahydro-pyrrolo[2,1-b]quinazoline (purity: 85%). The crude product is used in the next step without further purification.

b) A mixture of 3.85 g crude 1,2,3,9-tetrahydro-pyrrolo[2,1-b]quinazoline and 5 g 2-bromobenzaldehyde is heated to 160° C. with stirring for 2 hrs. The mixture solidifies at ambient temperature and is diluted with dichloromethane. 20 ml of methanol are added to the resulting mixture, the dichloromethane is distilled off, whereupon the product solidifies again. The resulting solid compound is isolated and washed with cold methanol. Yield: 2.25 g yellow crystals, melting point 203–204° C.

Analogously are obtained the following compounds of formula I-100 of table I and compound A-126:

TABLE I (I-100)

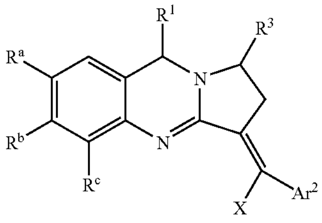

| Example | $R^a$ | $R^b$ | $R^c$ | $R^1$ | $R^3$ | X | $Ar^2$ | Physical Data |
|---|---|---|---|---|---|---|---|---|
| 102 | Br | H | Br | H | H | H | 2-chlorophenyl | mp. 214–219° C. |
| 103 | H | H | H | H | H | H | 2-chlorophenyl | mp. 190–191° C. |
| 104 | Br | $C(CH_3)_3$ | H | H | H | H | 2-chlorophenyl | oil |
| 105 | H | H | H | H | H | H | 2,6-dichlorophenyl | mp. 198–199° C. |
| 106 | H | H | H | H | H | H | 2-fluorophenyl | mp. 285° C. (HCl) |
| 107 | H | H | H | H | H | H | 2-chloro-4-dimethylaminophenyl | mp. >300° C. (2 HCl) |
| 108 | H | H | H | H | H | H | 2-trifluoromethyl-phenyl | mp. 109–110° C. (HCl) |
| 109 | H | H | H | H | $C_2H_5$ | H | 2-chlorophenyl | mp. 161–164° C. |
| 110 | H | H | H | H | H | H | 2-ethylphenyl | mp. 257° C. (HCl) |
| 111 | H | H | H | H | H | H | 4-dimethylamino-phenyl | mp. 205° C. |
| 112 | H | H | H | H | H | H | 3,4-dichlorophenyl | mp. 200° C. |
| 113 | H | H | H | H | H | H | 2-ethoxyphenyl | mp. 157–158° C. |
| 114 | H | H | H | H | H | H | thien-2-yl | mp. 208–210° C. |
| 115 | H | H | H | H | H | H | furan-2-yl | mp. 170° C. |
| 116 | H | H | H | H | H | H | thien-3-yl | mp. 208–209° C. |
| 117 | H | H | H | H | H | H | 1,1'-biphenyl-2-yl | mp. 255–256° C. (HCl) |
| 118 | H | H | H | H | H | H | 2-chloro-4-fluorophenyl | mp. 202–203° C. |
| 119 | H | H | H | H | H | H | 4-methoxy-3-methylphenyl | mp. 174–175° C. |

TABLE I-continued (I-100)

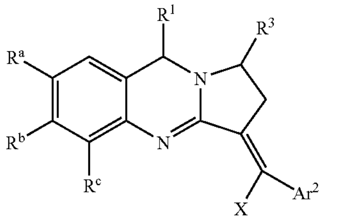

| Example | $R^a$ | $R^b$ | $R^c$ | $R^1$ | $R^3$ | X | $Ar^2$ | Physical Data |
|---|---|---|---|---|---|---|---|---|
| 120 | H | H | H | H | H | H | 2,4-dichlorophenyl | mp. 187–188° C. |
| 121 | H | H | H | H | H | $NH_2$ | 2-formylphenyl | mp. >270° C. (HCl) |
| 122 | H | H | H | H | H | H | 2-trifluoromethoxy-phenyl | mp. 225° C. (HCl) |
| 123 | H | H | H | H | 4-fluoro-phenyl | H | 2-bromophenyl | mp. 232–234° C. |
| 124 | H | H | H | H | H | H | 8-bromonaphth-1-yl | mp. 252–255° C. |
| 125 | H | H | H | H | n-butyl | H | 2-bromophenyl | mp. 151–154° C. |

EXAMPLE 126

6-(2-Chlorobenzylidene)-6,8,9,11-tetrahydro-7H-pyrido[2,1-b]quinazoline mp.: 242–248° C.

EXAMPLE 127

3-(2-Ethylbenzylidene)-1,2,3,9-tetrahydro-pyrrolo[2,1-b]quinazoline is obtained by hydrogenation of the compound of example 110 mp.: 224–225° C. (as hydrochloride)

EXAMPLE 201

3-(2-Bromobenzylidene)-9-imino-2,3-dihydro-1H-pyrrolo[2,1-b]quinazoline a) A mixture of 11.8 g 2-amino-benzonitrile and 13.6 g 5-methoxy-3,4-dihydro-2H-pyrrol is heated for 1.5 Std. at 120° C. and subsequently heated for 12 hrs. at 155° C. with stirring. Upon cooling down to ambient temperature the mixture is purified with flash-chromatography (silica gel, dichloromethane/methanol and 6 M $NH_3$ 97:3) to yield 6.65 g of 2,3-dihydro-1H-pyrrolo[2,1-b]quinazolin-9-ylideneamine, melting point: 129–130° C.

b) A mixture of 1 g 2.3-dihydro-1H-pyrrolo[2,1-b]quinazolin-9-ylideneamine and 1,.12 g 2-bromobenzaldehyde is heated for 3 hrs. at 160° C. with stirring, whereupon the product solidifies. Upon cooling 100 ml dichloromethane is added and 20 g silica gel is added to the resulting mixture. Dichloromethane is distilled off and the residue is purified with flash-chromatography (silica gel, dichloromethane/methanol 95:5) to yield. 0.18 g yellow crystals having a melting point of 205° C.

Analogously are obtained the following compounds of formula I-200 of table II and Example 215:

TABLE II (I-200)

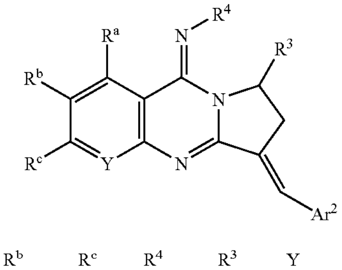

| Example | $R^a$ | $R^b$ | $R^c$ | $R^4$ | $R^3$ | Y | $Ar^2$ | Physical Data |
|---|---|---|---|---|---|---|---|---|
| 202 | H | H | H | H | H | CH | 2-chlorophenyl | mp. 202–203° C. |
| 203 | H | H | H | H | H | CH | 2-iodophenyl | amorphous solid |
| 204 | H | H | H | H | H | CH | 2-ethylphenyl | oil |
| 205 | H | H | H | H | H | CH | 4-methoxyphenyl | mp. 175–177° C. |
| 206 | H | $CH_3O$ | $CH_3O$ | H | H | CH | 2-bromophenyl | mp. 192–194° C. |
| 207 | F | H | H | H | H | CH | 2-bromophenyl | mp. 214–219° C. |
| 208 | H | H | H | H | H | N | 2-bromophenyl | mp. 232° C. |
| 209 | H | H | H | $CH_3$ | H | CH | 2-bromophenyl | mp. 149–150° C. |
| 210 | Cl | H | H | H | H | CH | 2-bromophenyl | mp. 189–191° C. |

TABLE II-continued (I-200)

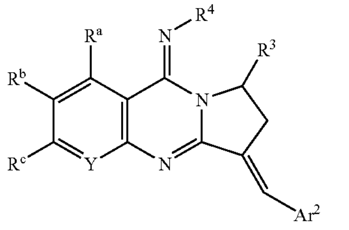

| Example | $R^a$ | $R^b$ | $R^c$ | $R^4$ | $R^3$ | Y | $Ar^2$ | Physical Data |
|---|---|---|---|---|---|---|---|---|
| 211 | $CH_3$ | H | H | H | H | CH | 2-bromophenyl | mp. 182–184° C. |
| 212 | H | H | H | CN | H | CH | 2-bromophenyl | mp. 260–261° C. |
| 213 | H | H | H | H | $CO_2CH_3$ | CH | 2-bromophenyl | mp. 181–182° C. |
| 214 | H | H | H | H | $CONH_2$ | CH | 2-bromophenyl | mp. 254° C. |

EXAMPLE 215

5-(2-Bromobenzylidene)-3,5,6,7-tetrahydro-1,3,4,7a-tetraaza-s-indazene-8-ylideneamine mp.: 260° C. as formiate

EXAMPLE 301

7-(2-Bromobenzylidene)-6,7-dihydro-5H-1-thia-4a,8-diazo-s-indacen-4-ylideneamine a) A mixture of 6.2 g 2-amino-3-cyano-thiophen and 5,95 g 5-methoxy-3,4-dihydro-2H-pyrrol are heated for 2 hrs. at 120° C. and 1 hr. at 155° C. with stirring. Upon cooling down to ambient temperature the mixture is diluted with acetone and solid particles are filtered off. The mixture is concentrated and methanol is added. The mixture is acidified with alcoholic HCl. Subsequently the product is precipitated by addition of diethylether and the crystals and dried to yield 4.5 g of 6,7-dihydro-5H-1-thia-4a,8-diaza-s-indacen-4-ylideneamine hydrochloride as light yellow crystals.

b) A mixture of 6,7-dihydro-5H-1-thia-4a,8-diaza-s-indacen-4-ylideneamine, dichlormethane and methanol is treated with concentrated NaOH to release the free base. A mixture of 0.96 g of this free base and 1.1 g 2-bromobenzaldehyde is heated for 1 hr. at 130° C. with stirring. Upon cooling down to ambient temperature the mixture is diluted with methanol. The crystals formed are separated, washed with methanol, dichloromethane and diethylether and dried to yield 1.3 g of (2-Bromophenyl)-(4-imino-4,5,6,7-tetrahydro-1-thia-4a,8-diaza-s-indacen-7-yl)-methanol as light brown crystals (melting point 228° C.).

c) A mixture of 0.8 g (2-Bromophenyl)-(4-imino-4,5,6,7-tetrahydro-1-thia-4a,8-diaza-s-indacen-7-yl)-methanol and 5 ml $POCl_3$ is heated for 2 hrs. at 150° C. Upon cooling down to ambient temperature ice water is added to the mixture and the prcipitate formed is separated. The solid product is suspended with water, treated with concentrated NaOH and extracted with dichloromethane. The organic phase is dried over $Na_2SO_4$, filtered and concentrated. The residue is stirred with acetone and the crystals are separated to yield 0.3 g of 7-(2-Bromobenzylidene)-6,7-dihydro-5H-1-thia-4a,8-diazo-s-indacen-4-ylideneamine as yellow crystalls (melting point 183–184° C.).

Analogously are obtained the following compounds of formula I-300 of table III:

TABLE III (I-300)

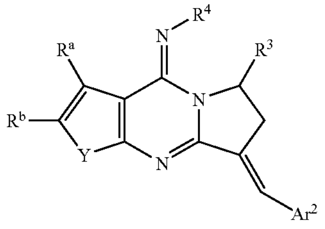

| Example | $R^a$ | $R^b$ | $R^4$ | Y | $Ar^2$ | Physical Data |
|---|---|---|---|---|---|---|
| 302 | $—(CH_2)_4—$ | | H | S | 2-bromophenyl | mp. 202–204° C. |
| 303 | $CH_3$ | $CH_3$ | H | S | 2-bromophenyl | mp. 180° C. |
| 304 | $C(CH_3)_3$ | H | H | S | 2-bromophenyl | mp. >280° C. |
| 305 | cyclopropyl | H | H | S | 2-bromophenyl | mp. 209° C. |
| 306 | $CH_3$ | $CH_3$ | H | O | 2-bromophenyl | mp. >290° C. |

Using the CCR3-Receptor Binding Protocol described hereinbefore, the affinities of the tested compounds according to the invention obtained are shown in Table IV, in which the affinities are rated as follows:

TABLE IV

| Example No. | Affinity |
|---|---|
| 101 | +++ |
| 102 | + |
| 103 | +++ |
| 104 | + |
| 105 | + |
| 106 | + |
| 107 | + |
| 108 | + |
| 109 | ++ |
| 110 | + |
| 111 | + |
| 112 | ++ |
| 113 | + |
| 114 | + |
| 115 | + |
| 116 | + |
| 117 | + |
| 118 | ++ |

TABLE IV-continued

| | |
|---|---|
| 119 | + |
| 120 | + |
| 122 | + |
| 123 | + |
| 124 | + |
| 125 | ++ |
| 126 | + |
| 127 | + |
| 201 | +++ |
| 202 | +++ |
| 203 | +++ |
| 204 | ++ |
| 205 | + |
| 206 | ++ |
| 207 | ++ |
| 208 | ++ |
| 209 | ++ |
| 210 | ++ |
| 211 | ++ |
| 212 | + |
| 213 | ++ |
| 214 | + |
| 301 | +++ |
| 302 | ++ |
| 303 | ++ |
| 304 | + |
| 305 | ++ |
| 306 | ++ |

| Affinity | Ki-value [nM] |
|---|---|
| +++ | 1–100 |
| ++ | 100–1000 |
| + | 1000–10,000 |

What is claimed is:

1. A compound of formula (I):

(I)

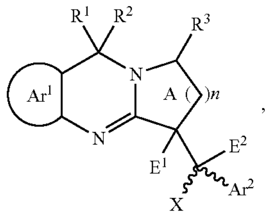

wherein $R^1$ and $R^2$ each independently represent a hydrogen atom, or a $C_1$–$C_6$-alkyl, $C_2$–$C_6$-alkenyl, $C_2$–$C_6$-alkinyl, $C_3$–$C_8$-cycloalkyl, $C_3$–$C_8$-cycloalkyl-$C_1$–$C_6$-alkyl, —$NH_2$, —NH($C_1$–$C_6$-alkyl), —N($C_1$–$C_6$-alkyl)$_2$, aryl or aryl-$C_1$–$C_6$-alkyl group, wherein any of these groups may optionally be substituted by one or more substituents selected from the group consisting of halogen, $OR^6$, $SR^6$, cyano, $COOR^6$, $CONR^6R^7$, $NR^6R^7$, $NR^6COR^5$, $SOR^6$, $SO_2R^6$ and $C_1$–$C_6$-haloalkyl, $R^1$ and $R^2$ together with the interjacent carbon atom form a 3- to 8-membered cycloalkyl ring, which may be substituted by one or more substituents selected from the group consisting of halogen, $C_1$–$C_6$-alkyl, $OR^6$, $SR^6$, cyano and $C_1$–$C_6$-haloalkyl or $R^1$ and $R^2$ form together a group $=NR^4$;

$R^3$ represents a hydrogen atom or a $C_1$–$C_{18}$-alkyl, $C_2$–$C_6$-alkenyl, $C_2$–$C_6$-alkinyl, $C_3$–$C_8$-cycloalkyl, $C_3$–$C_8$-cycloalkyl-$C_1$–$C_6$-alkyl, aryl, or aryl-$C_1$–$C_6$-alkyl, $COOR^5$, $CR^6R^7OH$ or $CONR^6R^7$ group, wherein any of these groups may optionally be substituted by one or more substituents selected from the group consisting of halogen, $OR^6$, $SR^6$, CN, $COOR^6$, $CONR^6R^7$, $NR^6R^7$, $NR^6COR^5$, $SOR^6$, $SO_2R^6$ and $C_1$–$C_6$-haloalkyl;

$R^4$ represents a hydrogen atom or a $COOR^5$, $COR^5$, $OR^6$, cyano or nitro group; or a $C_1$–$C_6$-alkyl group, which, may optionally be substituted by one or more substituents selected from the group consisting of halogen, $OR^6$, $SR^6$, CN, $COOR^6$, $CONR^6R^7$, $NR^6R^7$, $NR^6COR^5$, $SOR^6$, $SO_2R^6$ and $C_1$–$C_6$-haloalkyl; or $R^2$ and $R^3$ together with the interjacent group —$CR^1$—N—CH— form a 5- to 8-membered ring; or $R^3$ and $R^4$ together with the interjacent group —N═C—N—CH— form a 5- to 8-membered ring;

$R^5$ represents a hydrogen atom or a $C_1$–$C_{18}$-alkyl, $C_2$–$C_6$-alkenyl, $C_2$–$C_6$-alkinyl, $C_3$–$C_8$-cycloalkyl, $C_3$–$C_8$-cycloalkyl-$C_1$–$C_6$-alkyl, aryl or aryl-$C_1$–$C_6$-alkyl group, wherein any of these groups may optionally be substituted by one or more substituents selected from the group consisting of halogen, $OR^6$, $SR^6$, CN, $COOR^6$, $CONR^6R^7$, $NR^6R^7$, $NR^6COR^5$, $SOR^6$, $SO_2R^6$ and $C_1$–$C_6$-haloalkyl;

$R^6$ and $R^7$ each independently represent a hydrogen atom, or a $C_1$–$C_{18}$-alkyl, $C_3$–$C_8$-cycloalkyl aryl or aryl-$C_1$–$C_6$-alkyl group; or $R^6$ and $R^7$ together with the interjacent nitrogen atom form a 3–8-membered heterocyclic ring;

$E^1$ and $E^2$ each represent a hydrogen atom or taken together form a double bond;

X represents a hydrogen or halogen atom, or a $C_1$–$C_6$-alkyl, $C_2$–$C_6$-alkenyl, $C_2$–$C_6$-alkinyl, $C_3$–$C_8$-cycloalkyl, $C_3$–$C_8$-cycloalkyl-$C_1$–$C_6$-alkyl, $OR^6$, $SR^6$, $NR^6R^7$ or aryl;

the ring A may be substituted by one or more group $R^6$;

Aryl, $Ar^1$ and $Ar^2$ each independently represent a 6- to 10-membered homoaromatic group or a 5- to 10-membered heteroaromatic group containing up to three heteroatoms selected from the group consisting of nitrogen, oxygen and sulfur; wherein each of these groups may be substituted by one or more substituents selected from the group consisting of $C_1$–$C_6$-alkyl, phenyl, halogen, $OR^6$, $SR^6$, cyano, nitro, $COOR^6$, $COR^6$, $CONR^6R^7$, $NR^6R^7$, $NR^6COR^5$, $NR^6SO_2R^5$, $SOR^6$, $SO_2R^6$, $SO_2NR^6R^7$, $C_1$–$C_6$-haloalkyl, $C_1$–$C_6$-haloalkoxy and $C_3$–$C_8$-cycloalkyl; and n represents 1, or the pharmaceutically acceptable salts thereof.

2. The compound of formula I according to claim 1, wherein

Aryl, $Ar^1$ and $Ar^2$ each independently are selected from the group consisting of phenyl, thienyl, furanyl, pyrrolyl, pyridyl, pyrimidyl, naphthyl, benzothiophenyl, indolyl, thiazolyl, oxazolyl and imidazolyl, wherein each of these groups may be substituted by one two or three substituents selected from the group consisting of $C_1$–$C_6$-alkyl, halogen, $OR^6$, $SR^6$, cyano, nitro, $COOR^6$, $COR^6$, $CONR^6R^7$, $NR^6R^7$, $NR^6COR^5$, $NR^6SO_2R^5$, $SOR^6$, $SO_2R^6$, $SO_2NR^6R^7$, $C_1$–$C_6$-haloalkyl, $C_1$–$C_6$-haloalkoxy and $C_3$–$C_8$-cycloalkyl.

3. The compound of formula I according to claim 2, wherein wherein $R^1$ and $R^2$ each independently represent a hydrogen atom, or a $C_1$–$C_6$-alkyl group, $R^1$ and $R^2$ form together a group $=NR^4$;

$R^3$ represents a hydrogen atom or a $C_1$–$C_{18}$-alkyl group, $R^4$ represents a hydrogen atom, or a $C_1$–$C_6$-alkyl or cyano group, $E^1$ and $E^2$ taken together form a double bond;

$Ar^1$ represents a phenyl, thiophene or furane group, which may be substituted by one or more substituents selected from the group consisting of $C_1$–$C_6$-alkyl, halogen, $OR^6$, $SR^6$, cyano, nitro, $COOR^6$, $COR^6$, $CONR^6R^7$, $NR^6R^7NR^6COR^5$, $NR^6SO_2R^5$, $SOR^6$, $SO_2R^6$, $SO_2NR^6R^7$, $C_1$–$C_6$-haloalkyl and $C_3$–$C_8$-cycloalkyl, $Ar^2$ represents a phenyl, thienyl or furanyl group, which may be substituted by one or more substituents selected from the group consisting of $C_1$–$C_6$-alkyl, halogen, $OR^6$, $SR^6$, cyano, nitro, $COOR^6$, $COR^6$, $CONR^6R^7$, $NR^6R^7$, $NR^6COR^5$, $NR^6SO_2R^5$, $SOR^6SO_2R^6$, $SO_2NR^6R^7$, $C_1$–$C_6$-haloalkyl, $C_1$–$C_6$-haloalkoxy and $C_3$–$C_8$-cycloalkyl.

4. The compound of formula I according to claim 3, wherein $R^1$ and $R^2$ represent a hydrogen atom, or $R^1$ and $R^2$ form together a group $=NR^4$;

$R^3$ and $R^4$ each independently represent a hydrogen atom or a $C_1$–$C_6$-alkyl group, $E^1$ and $E^2$ taken together form a double bond;

$Ar^1$ represents a phenyl, thiophene or furane group, which may be substituted by one or more substituents selected from the group consisting of $C_1$–$C_6$-alkyl, halogen, $C_1$–$C_6$-haloalkyl and $C_3$–$C_6$-cycloalkyl, $Ar^2$ represents a phenyl, thienyl or furanyl group, which may be substituted by a halogen atom, and X represents a hydrogen atom.

5. The compound of formula I according to claim 4, wherein $Ar^2$ represents a phenyl, thienyl or furanyl group, which is substituted by a halogen atom, in the ortho position.

6. A method of treating asthma, comprising administering to a patient a pharmaceutically effective amount of a compound according to claim 1.

7. A Pharmaceutical composition comprising a pharmaceutically effective amount of a compound of formula (I) according to claim 1.

8. A Process of preparing a compound of formula (I) according to claim 1, comprising:

reacting at a temperature of 160° C. for 2 hours a compound of formula (II)

(II)

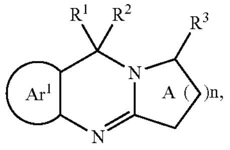

wherein $Ar^1$, A, $R^1$, $R^2$, $R^3$ and n have the meaning given in claim 1, with a compound of formula (III)

(II)

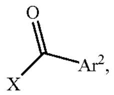

wherein $Ar^2$ and X have the meaning given in claim 1 and wherein if $E^1$ and $E^2$ are hydrogen atoms then optionally hydrogenating;

cooling to ambient temperature and subsequently isolating the product compound.

* * * * *